(12) United States Patent
Kagaya (10) Patent No.: US 8,228,376 B2
(45) Date of Patent: Jul. 24, 2012

(54) IMAGE TAKING APPARATUS

(75) Inventor: Makoto Kagaya, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 987 days.

(21) Appl. No.: 12/196,598

(22) Filed: Aug. 22, 2008

(65) Prior Publication Data
US 2009/0058998 A1   Mar. 5, 2009

(30) Foreign Application Priority Data
Aug. 30, 2007   (JP) ................. 2007-224104

(51) Int. Cl.
*A61B 1/04* (2006.01)
*A61B 1/00* (2006.01)

(52) U.S. Cl. ........................... 348/68; 600/101

(58) Field of Classification Search ...... 348/68
See application file for complete search history.

(56) References Cited

U.S. PATENT DOCUMENTS

| | | | |
|---|---|---|---|
| 4,729,018 A * | 3/1988 | Watanabe et al. | 348/69 |
| 6,540,671 B1 * | 4/2003 | Abe et al. | 600/180 |
| 2002/0175993 A1 * | 11/2002 | Ueno et al. | 348/68 |
| 2007/0076975 A1 * | 4/2007 | Abe | 382/274 |
| 2007/0223797 A1 * | 9/2007 | Kaneko | 382/128 |

FOREIGN PATENT DOCUMENTS

JP   05-228110 A   9/1993

* cited by examiner

*Primary Examiner* — Firmin Backer
*Assistant Examiner* — James Edwards
(74) *Attorney, Agent, or Firm* — Sughrue Mion, PLLC (57) ABSTRACT

The image taking apparatus includes: a CCD which takes an image of a subject to obtain a shot image; a processor-side CPU which has three or more photometric modes having different analysis schemes to measure brightness of the shot image by analyzing the shot image taken by the CCD; and an aperture for reducing light from a light source based on the brightness measured by the processor-side CPU. In the processor-side CPU, two or more of the photometric modes corresponding to a selecting operation are selected, and one of the selected photometric modes is cyclically switched between the selected photometric modes upon reception of the switching operation instructing the switching.

9 Claims, 4 Drawing Sheets

IMAGE TAKING APPARATUS

BACKGROUND OF THE INVENTION

1. Field of the Invention

The present invention relates to an image taking apparatus which shoots an image of a subject to obtain a shot image.

2. Description of the Related Art

Conventionally, in a medical field, there is widely used an endoscope apparatus in which a thin and long tube provided at its tip end with a CCD is inserted into a body of a subject being examined and an image in the body of the subject being examined is shot to observe tumor or cerebral thrombosis. According to such an endoscope apparatus, if the inside of the body of the subject being examined is directly shot, it is possible to grasp color or state of nidus that can not easily be observed by a radiation image without externally damaging the subject being examined, allowing easily obtaining of information necessary for determining a course of remedy.

According to such an endoscope apparatus, the inside of the body of the subject being examined is lighted and under this lighted condition, an image in the body is taken. To avoid illumination inconvenience such as halation, generally brightness of a shot image is measured, i.e., photometry, by analyzing the shot image. The illumination for brightening the inside of the body of the subject being examined is adjusted to an appropriate brightness based on the brightness obtained by the photometry.

Here, there are various known analyzing methods in photometry such as an average photometry and a peak photometry. In the average photometry, the average of brightness at locations in a shot image is defined as the brightness of the shot image, while in the peak photometry, brightness of high brightness portion in the shot image is defined as the brightness of the shot image. In many cases, an analyzing method suitable for adjusting the brightness in the picture taking using the endoscope apparatus is varied depending upon a preference of a user who operates the endoscope apparatus and shooting environment. Hence, some endoscope apparatuses have a number of photometric modes having different analyzing methods so that a user can select a desired photometric mode.

When the endoscope apparatus of such a structure is used at a medical site, a user frequently changes a photometric mode to another mode while operating the endoscope apparatus. To enhance the operability, there is proposed an endoscope apparatus which cyclically switches between a plurality of selectable photometric modes by pushing a button upon receiving a pushing operation of a button at a user's hand (see Japanese Patent Application Publication No. 5-228110 for example).

According to the endoscope apparatus described in Japanese Patent Application Publication No. 5-228110, however, since the switching is carried out by pushing the button cyclically, if an unnecessary photometric mode totally unnecessary for a user exists, such unnecessary photometric mode should be pushed to reach a desired photometric mode from the current mode, which is troublesome for a user.

This problem is not limited to the endoscope apparatus, but is common with an image taking apparatus in which a picture is taken while the shooting condition is adjusted by the photometry and the photometric modes are cyclically switched.

SUMMARY OF THE INVENTION

In view of the above circumstances, the present invention provides an image taking apparatus in which switching between photometric modes is easily performed.

An image taking apparatus according to the present invention includes:

a shooting section which takes an image of a subject to obtain a shot image;

a photometric section which has three or more photometric modes each having a different analysis scheme for analyzing the shot image taken by the shooting section and thereby measuring brightness of the shot image;

a condition adjuster which adjusts a shooting condition affected by brightness of the shot image, based on the brightness measured by the photometric section;

a mode selector which selects two or more photometric modes in accordance with a selecting operation from the three or more photometric modes of the photometric section; and a mode switcher which allows the photometric section to execute one of the photometric modes selected by the mode selector, and cyclically switches the one of the photometric modes between the photometric modes selected by the mode selector, in response to a switching operation for instructing switching of the photometric mode.

According to the image taking apparatus of the present invention, the two or more photometric modes selected by the mode selector are switched cyclically. The two or more photometric modes are selected by the mode selector in accordance with the selecting operation. According to the image taking apparatus of the invention, a user can select two or more photometric modes, which are assumed by a user to be necessary at the time of shooting, by means of the selecting operation before shooting, and the user can cyclically switch between only the necessary photometric modes at the time of shooting. That is, according to the image taking apparatus of the invention, it is possible to switch between the photometric modes without passing through unnecessary photometric mode with easy operation.

Here, it is preferable that the image taking apparatus according to the present invention further includes:

a light source; and a light-introducing section which introduces light emitted from the light source to the subject, wherein the condition adjuster adjusts an amount of light passing through any of optical paths extending from the light source to the shooting section through the subject.

This typical feature is suitable for an endoscope apparatus which illuminates a subject with light emitted from the light source to take a picture. The brightness of the illumination for the subject is adjusted by reducing the amount of light emitted from the light source between the light source and the light-introducing section.

Further preferably, the image taking apparatus according to the present invention includes:

a dual-purpose operating element used for both the selecting operation and the switching operation, and an operation changing section which changes operation of the dual-purpose operating element between the selecting operation and the switching operation, in response to a changing operation for instructing change of operation of the dual-purpose operating element.

According to the image taking apparatus of the preferred feature, since both the selecting operation and switching operation can be carried out using the dual-purpose operating element, it is possible to more easily switch between the photometric modes.

Also in the image taking apparatus according to the present invention, the mode switcher may allow the photometric section to execute one of the three or more photometric modes, in response to an expansion operation for instructing expansion of a range of switchable photometric modes, and changes the switching of the one of the photometric modes by the switching operation to a cyclical switching between the three or more photometric modes.

According to the image taking apparatus with this preferable feature, it is possible to easily change the operation state by the expansion operation even when a user wants to stop switching between the two or more photometric modes and desires to switch between all of photometric modes which can be executed by the image taking apparatus.

In addition, the image taking apparatus according to the present invention may further include a display section which displays the shot image obtained by the shooting section, which also displays the photometric modes selected by the mode selector, and which displays the photometric mode executed by the photometric section among the selected photometric modes in a display mode different from that of other photometric modes.

According to the image taking apparatus with this preferable feature, a user can easily visually know what the current photometric mode is and to which photometric mode the current photometric mode can be switched, based on the display of the photometric mode by the display section.

The image taking apparatus according to the present invention, may further include a body having at least the photometric section and the mode selector, and a scope which is detachably attached to the body and which has at least the shooting section and a mode storing section which stores the photometric modes selected by the mode selector, wherein when the scope is attached to the body, the mode selector captures the photometric modes stored in the mode storing section as photometric modes selected by the mode selector.

According to the image taking apparatus with this preferable feature, after the two or more photometric modes are stored by the mode storing section of the scope, a switching population is automatically set to the stored two or more photometric modes. Therefore, it is possible to more easily switch the photometric mode.

Further preferably, in the image taking apparatus according to the present invention, wherein the mode selector includes an operation selecting mode for selecting photometric modes in accordance with the selecting operation, and an automatically selecting mode for capturing the photometric modes stored in the mode storing section as photometric modes selected by the mode selector, and the operation selecting mode and the automatically selecting mode can be switched to each other by operation.

According to the image taking apparatus with this preferable feature, when a user desires to switch in a population that is different from an automatically set population, the selection by the mode selector is switched to the operation selecting mode. With this, a desired population can be set.

Preferably, the image taking apparatus according to the present invention, further includes:

a body having at least the photometric section and the mode selector; and a scope which has at least the shooting section and which is detachably attached to the body, the scope having a model storing section which stores a model of the scope, wherein the body has a model-associated mode storing section which stores photometric modes selected by the mode selector in association with a model of the scope attached to the body, and wherein when the body is attached to the scope, the mode selector captures the photometric modes which are stored in the model-associated mode storing section associated with the same model as that of the scope, as the photometric modes selected by the mode selector.

According to the image taking apparatus with this preferable feature, after the two or more photometric modes are stored by the model-associated mode storing section, for a scope of the same model as that of the scope in which the two or more photometric modes were stored, the switching population is automatically set to the stored two or more photometric modes. Thus, it is possible to more easily switch between the photometric modes.

In addition, in the image taking apparatus according to the present invention, the mode selector may include an operation selecting mode for selecting photometric modes in accordance with the selecting operation, and a model-associated selection mode for capturing the photometric modes stored in the model-associated mode storing section as the photometric modes selected by the mode selector, and wherein the operation selecting mode and the model-associated selection mode can be switched to each other by operation.

According to the image taking apparatus of this preferable mode, when a user desires to switch between populations which are different from automatically set populations, the selection of the mode selector is switched to the operation selecting mode. With this, a desired population can be set.

As described above, according to the present invention, it is possible to provide an image taking apparatus in which switching between photometric modes is easily performed.

DETAILED DESCRIPTION OF THE INVENTION

An embodiment of the present invention will be described with reference to the drawings.

Figure 1:
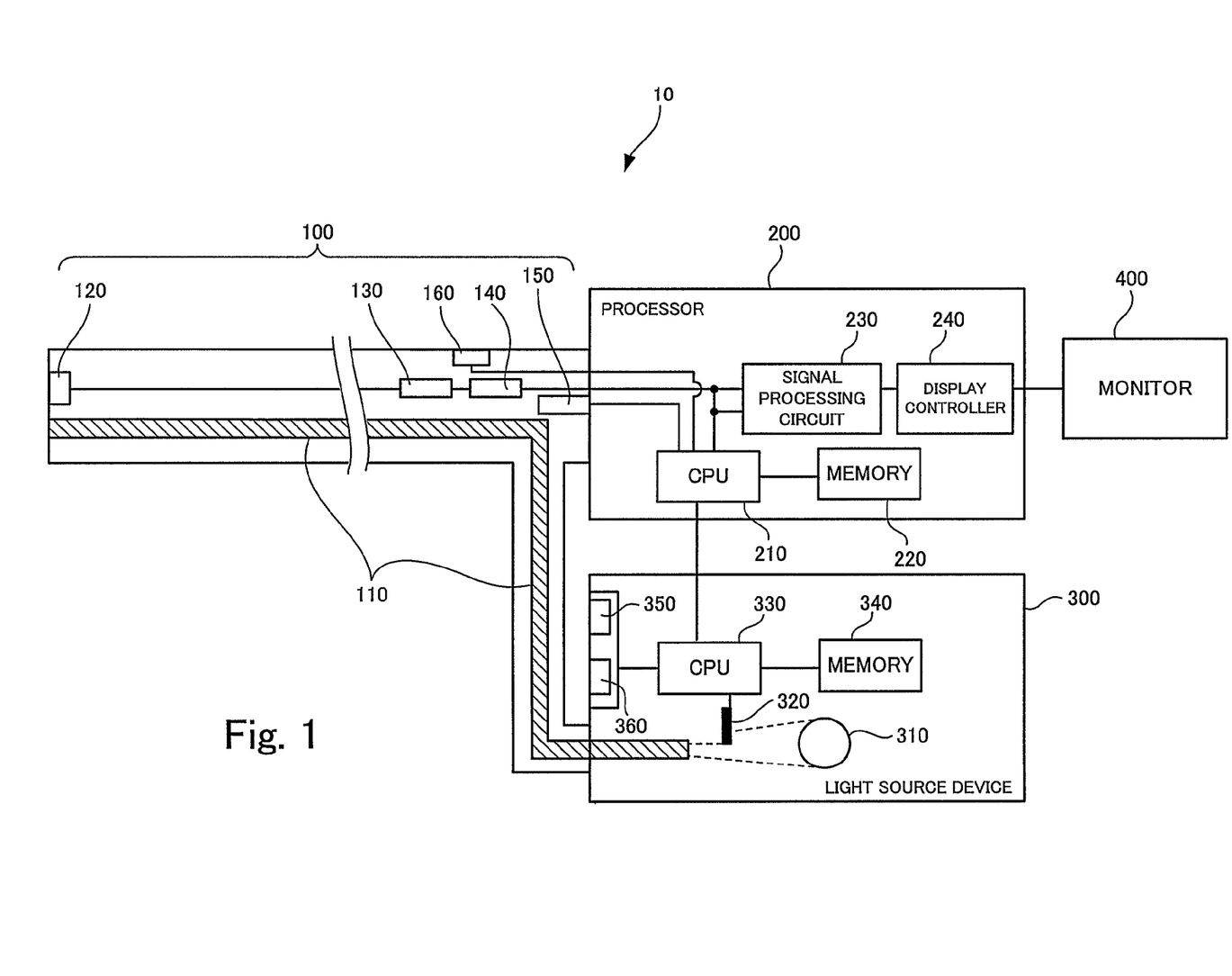
FIG. 1 is a diagram showing an endoscope apparatus according to an embodiment of the present invention.

FIG. 1 is a diagram showing an endoscope apparatus according to an embodiment of the present invention.

The endoscope apparatus 10 shown in FIG. 1 corresponds to one example of an image taking apparatus according to the present invention. The endoscope apparatus 10 includes a scope 100 which is inserted into a subject being examined to illuminate a subject therein, take an image thereof under illumination to obtain a shot image, a processor 200 which performs various image processing to the shot image obtained by the scope 100, a light source device 300 which supplies illumination light to the scope 100, and a monitor 400 for displaying a shot image to which the image processing has been performed in the processor 200. The scope 100 corresponds to one example of the scope according to the invention, and a combination of the processor 200 and the light source device 300 corresponds to one example of the body according to the invention.

The scope 100 is detachably attached to the processor 200 and the light source device 300, and includes an optical fiber light guide 110 and a CCD 120 for shooting a subject. The light guide 110 introduces illumination light supplied from the light source device 300 to a photographic object in a subject being examined. The CCD 120 receives light reflected by the object under illumination of the introduced light, thereby producing analog image data of a moving image representing an image of the object. The scope 100 further includes a CDS/AGC circuit 130 which carries out correlation double sampling (CDS) and an automatic gain control (AGC) for appropriately amplifying analog data, and an A/D converting circuit 140 which converts analog data to digital data. Animation analog image data produced by the CCD 120 is sent to the A/D converting circuit 140 through the CDS and the AGC and is converted into moving image digital image data. The digital image data of the moving image is sent to the processor 200. The light guide 110 corresponds to one example of the light-introducing section according to the invention, and a combination of the CCD 120, the CDS/AGC circuit 130 and the A/D converting circuit 140 correspond to one example of the shooting section according to the invention. The scope 100 also includes an EEPROM 150 which stores various information such as models of the scopes 100.

The processor 200 includes a processor-side CPU 210 which controls the entire endoscope apparatus 10 including action of each constituent element of the scope 100, and a processor-side memory 220 which stores various control programs and various information required for control. The processor 200 also includes a signal processing circuit 230 which carries out various image processing such as gamma correction and color saturation correction for images by instructions from the processor-side CPU 210, and a display controller 240 for displaying, on the monitor 400, images to which various image processing are performed by the signal processing circuit 230.

In the processor 200, the digital image data for the moving image sent from the scope 100 is input to the signal processing circuit 230, moving image represented by the digital image data is subjected to the various image processing, and the processed moving image represented by the digital image data is displayed on the monitor 400 by the display controller 240. The signal processing circuit 230 and the processor-side CPU 210 also relates to the adjustment of light to be supplied to the scope 100, which will be described in detail later.

The light source device 300 includes a light source 310, and an aperture 320 which adjusts an amount of light emitted from the light source 310 toward the light guide 110 of the scope 100. In this embodiment, the aperture 320 is disposed such that the aperture 320 can rotate around a rotation axis (not shown) in a direction intersecting with a light path from the light source 310 to the light guide 110. The amount of light emitted from the light source 310 to the light guide 110 is an amount corresponding to how much the light path is blocked by the aperture 320 after rotation, i.e., an amount corresponding to a rotation amount of the aperture 320. The light source device 300 also includes a light source device-side CPU 330 which controls the entire action of the light source device 300, and a light source device-side memory 340 which stores various information required for various control programs and control. The amount of rotation of the aperture 320 is controlled by the light source device-side CPU 330. The light source 310 corresponds to one example of the light source according to the present invention.

The adjustment of the amount of light from the light source 310 to the light guide 110 by the control of the rotation amount of the aperture 320 will be described.

In the signal processing circuit 230 of the processor 200, a static image is appropriately extracted from a number of shot images constituting the moving image represented by digital image data. In the signal processing circuit 230, a histogram concerning brightness of each of locations in the extracted static image is prepared. The prepared histogram is delivered to the processor-side CPU 210. The processor-side CPU 210 analyzes the histogram and calculates brightness of the static image extracted by the signal processing circuit 230.

The processing from preparation of the histogram by the signal processing circuit 230 to the calculation of brightness by the processor-side CPU 210 corresponds to the photometry of the extracted static image, and a combination of the processor-side CPU 210 and the signal processing circuit 230 corresponds to one example of the photometric section according to the present invention.

Here, in this embodiment, the following three photometric modes having different calculation methods of brightness by analysis of a histogram by the processor-side CPU 210 are prepared for the photometry. The three photometric modes are: an average photometric mode in which the average value of brightness in a histogram is calculated as brightness of the extracted static image; a peak photometric mode in which brightness at which a cumulative degree from high brightness in a histogram becomes equal to a predetermined value (10% in this example) is calculated as brightness of the static image; and a mix photometric mode in which the calculation result of the average photometry and the calculation result of the peak photometric mode are each multiplied by 0.5 weight and are added, and this result is calculated as brightness of the static image.

The photometry is carried out in one of these three photometric modes desired by a user. As an operating element which is operated in connection with setting of a photometric mode desired by a user, the scope 100 is provided with a scope-side operation button 160, and the light source device 300 is provided with a light source device-side first operation button 350 and a light source device-side second operation button 360. Setting of photometric modes using these buttons will be described in detail later.

Brightness obtained by a photometry carried out in a desired photometric mode is delivered to the light source device-side CPU 330 from the processor-side CPU 210.

The light source device-side CPU 330 determines whether brightness delivered from the processor-side CPU 210 is within a predetermined permissible region. If the delivered brightness is not within the permissible range, the light source device-side CPU 330 calculates the rotation amount of the aperture 320 based on a difference between the delivered brightness and the permissible range, and moves a position of the aperture 320 in accordance with the calculation result. The rotation amount of the aperture 320 corresponds to one example of the shooting condition according to the present invention, and a combination of the aperture 320 and the light source device-side CPU 330 which moves the aperture 320 corresponds to one example of the condition adjuster according to the present invention.

In this embodiment, extraction and photometry of a shot image, and rotation of the aperture 320 are repeated at predetermined intervals during shooting operation by the endoscope apparatus 10. With this, the brightness of moving image displayed on the monitor is maintained at a value within the permissible range.

Next, setting of a photometric mode will be described.

The endoscope apparatus 10 shown in FIG. 1, at its default, can selectively set one of the three photometric modes, i.e., the peak photometric mode, the average photometric mode and the mix photometric mode. In this default state, a desired photometric mode is set by cyclically switching between the three photometric modes in the order of the peak photometric mode, the average photometric mode and the mix photometric mode. This cyclical switching is carried out by pushing the scope-side operation button 160 in the scope 100, and by pushing the light source device-side first operation button 350 in the light source device 300. That is, whenever a user pushes these buttons, the processor-side CPU 210 cyclically switches between the photometric modes, from the peak photometric mode to the average photometric mode, from the average photometric mode to the mix photometric mode, and from the mix photometric mode to the peak photometric mode.

In the default state, since the switching of the photometric modes is carried out in all of the three photometric modes, this default state is troublesome for a user who uses only two of the photometric modes because a desired photometric mode can not be obtained without passing through the unnecessary photometric mode. Hence, in this embodiment, a user can previously set a combination of two or more photometric modes which will be actually used. The combination of the photometric modes is set by pushing the light source device-side second operation button 360 of the light source device 300. If the light source device-side second operation button 360 is pushed, the following setting screen is displayed on the monitor 400.

Figure 2:
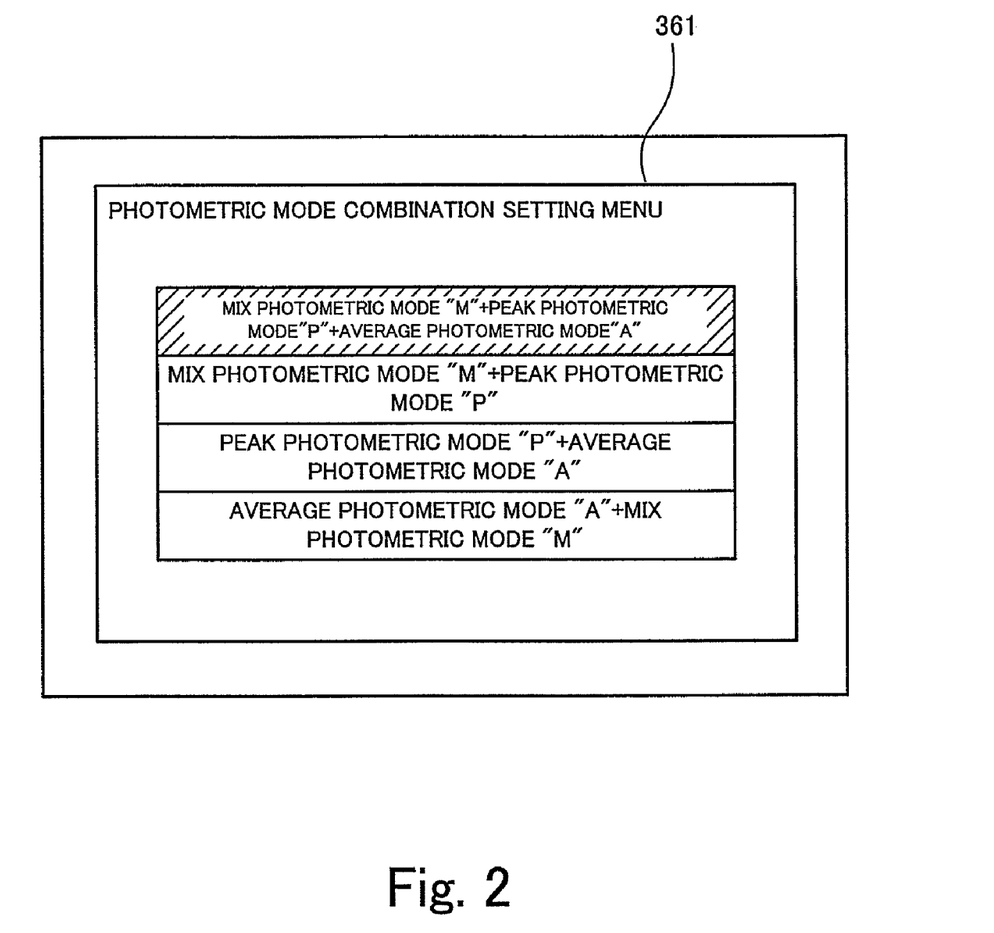
FIG. 2 is a diagram showing a setting screen for previously setting a combination of two or more photometric modes intended to be used.

FIG. 2 shows a setting screen for presetting a combination of two or more photometric modes which will actually be used.

The light source device-side second operation button 360 is pushed, and a photometric mode combination setting menu 361 is displayed on the monitor 400 as the setting screen. In the photometric mode combination setting menu 361, there are displayed all of combinations (four kinds in total) of two or more photometric modes in the three photometric modes which can be executed by the endoscope apparatus 10. A combination of the photometric modes which are set when the light source device-side second operation button 360 is pushed is displayed in gray. If the light source device-side second operation button 360 is pushed in the default state, since all of the three photometric modes can be used, a description column of a combination of the three photometric modes is displayed in gray.

If the photometric mode combination setting menu 361 is displayed, in this embodiment, the description column which is displayed in gray, i.e., a combination which is to be set is cyclically switched in descending order in the drawing whenever a user pushes the light source device-side second operation button 360. If the user pushes the light source device-side second operation button 360 for a long time while displaying a desired combination of the description column in gray, a photometric mode forming the combination of that description column is selected from the three photometric modes in the processor-side CPU 210, and this combination is set. Here, serial numbers are allocated to combinations in the photometric mode combination setting menu 361 in the descending order in the drawing. If desired one of combinations is set, a serial number corresponding to the set combination is stored in the EEPROM 150 of the scope 100 shown in FIG. 1.

The series of operations for setting two or more combinations of the photometric modes described above for the light source device-side second operation button 360 correspond to one example of the selecting operation according to the present invention, and the processor-side CPU 210 which sets two or more combinations by selecting a photometric mode in accordance with the series of operations from the three photometric modes corresponds to one example of the mode selector according to the present invention. The EEPROM 150 corresponds to one example of the mode storing section according to the present invention.

In the embodiment, there are provided two operation buttons, i.e., the light source device-side second operation button 360 for setting the combination of the photometric modes and the light source device-side first operation button 350 for switching the photometric mode. However, the present invention is not limited to this embodiment, and it is possible to employ another embodiment in which one operation button used both for setting the combination of the photometric modes and for switching between the photometric modes is provided. This other embodiment will be described below.

Even if this embodiment is employed, a structure of the endoscope apparatus itself is the same except that the number of operation button of the light source device 300 is one. Therefore, this other embodiment will be described also with reference to FIG. 1.

In this other embodiment, upon receiving long pushing operation of the one operation button by a user, the processor-side CPU 210 changes the operation of the one operation button as follows.

If a user long-pushes the one operation button, the processor-side CPU 210 changes the operation of the one operation button between a setting operation of a combination of photometric modes and a switching operation of photometric modes.

If the one operation button is long-pushed in a state where the operation button is used for the setting operation of a combination of the photometric modes, a combination which is displayed in gray is set, and the processor-side CPU 210 changes the operation for the one operation button to the switching operation of photometric modes. If the one operation button is long-pushed in a state where the operation button is used for the switching operation of photometric modes, on the other hand, the processor-side CPU 210 changes the operation for the one operation button to the setting operation of combination of photometric modes. Here, the one operation button corresponds to one example of the dual-purpose operating element, and the processor-side CPU 210 corresponds to one example of a combination of the mode switcher and the operation changing section according to the present invention. The setting operation of a combination of photometric modes mentioned here corresponds to one example of the selecting operation according to the present invention.

This other embodiment has a merit that the number of buttons of the light source device 300 is smaller.

The explanation of this other embodiment is completed, and explanation of the original embodiment in which the light source device 300 is provided with the two operation buttons will be continued.

If the combination of the photometric modes is set in this manner, the switching between the photometric modes which is carried out by pushing the scope-side operation button 160 or the light source device-side first operation button 350 is restricted to the range of the set combination. That is, when a combination of the mix photometric mode and the peak photometric mode is set, the mix photometric mode is switched to the peak photometric mode, or the peak photometric mode is switched to the mix photometric mode without passing through the average photometric mode. That is, if a combination of two or more photometric modes which will actually be used is previously set, the photometric modes can be switched without passing through an unnecessary photometric mode.

Here, the pushing operation of the scope-side operation button 160 or the light source device-side first operation button 350 for switching between the photometric modes in the set combination corresponds to one example of the switching operation according to the present invention, and the processor-side CPU 210 which cyclically switches between the photometric modes in the range of the set combination whenever these buttons are pushed corresponds to one example of the mode switcher according to the present invention.

When the setting of a combination of photometric modes is completed, the display controller 240 shown in FIG. 1 changes the display on the monitor 400 from the photometric combination setting menu 361 in FIG. 2 to a moving image which is obtained by the shooting operation of the scope 100 and which is represented by digital image signals processed by the signal processing circuit 230. At that time, the display controller 240 displays a currently set combination of photometric modes on the monitor 400.

Figure 3:
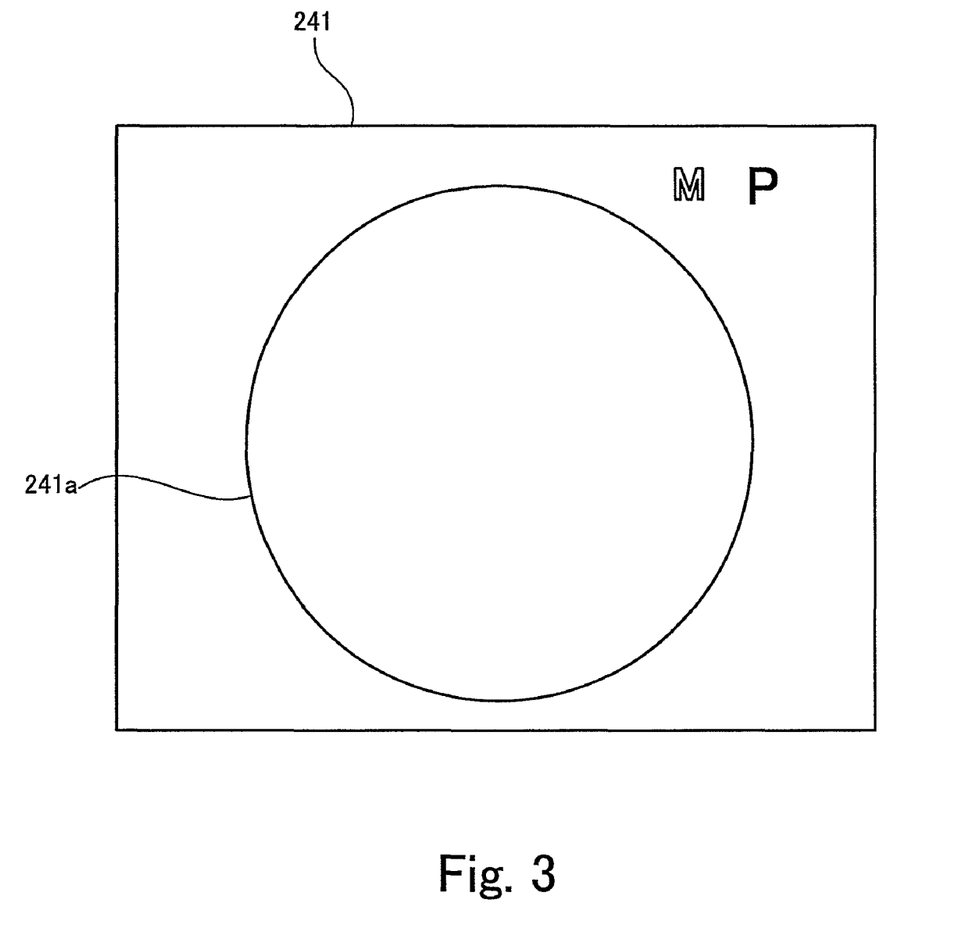
FIG. 3 is a schematic diagram showing one example of a display section after a combination of photometric modes is set.

FIG. 3 is a schematic diagram showing a display screen after setting of a combination of photometric modes is completed.

In this embodiment, a moving image is displayed in a central circular region 241*a* of a display screen 241 shown in FIG. 3. A currently set combination of photometric modes is shown in the upper right of the circular 241*a* of the drawing, with alphabets each indicating the relevant photometric mode. At that time, an alphabet corresponding to a photometric mode currently set by the switching operation is displayed with a color different from an alphabet corresponding to a photometric mode other than the currently set photometric mode. In the example shown in FIG. 3, a combination of the mix photometric mode and the peak photometric mode is currently set as a combination of photometric modes, with "M" indicating the mix photometric mode and "P" indicating the peak photometric mode. In the example in FIG. 3, the peak photometric mode among these photometric modes is currently set, "P" showing the peak photometric mode is displayed in a colored character, and "M" showing the mix photometric mode is displayed in an outline character on a colored background. If the scope-side operation button 160 or the light source device-side first operation button 350 is pushed in this state, the color of displayed character is exchanged with each other, "M" showing the mix photometric mode is displayed in the colored character and "P" showing the peak photometric mode is displayed in an outline character on a colored background. By displaying the character in this manner, a user can visually identify the currently combination of photometric modes and the current photometric mode at a glance.

The endoscope apparatus 10 shown in FIG. 1 has a function to change the switching of photometric modes from switching in a combination photometric modes that has been already set, to switching between all of three photometric modes. In this embodiment, this function is realized in such a manner that if a user long-pushes the scope-side operation button 160 or the light source device-side first operation button 350, the processor-side CPU 210 changes operations of the scope-side operation button 160 and the light source device-side first operation button 350 in the following manner. Here, the long-push of the scope-side operation button 160 or the light source device-side first operation button 350 corresponds to one example of the extension operation according to the present invention.

If a user long-pushes the scope-side operation button 160 or the light source device-side first operation button 350 after a combination of photometric modes is set, the processor-side CPU 210 changes the operations of the scope-side operation button 160 or the light source device-side first operation button 350, from the switching operation in the combination of the photometric modes, to the switching operation in the three photometric modes corresponding to the default state. Then, if the scope-side operation button 160 or the light source device-side first operation button 350 is long-pushed, the operations of the buttons are returned from the switching operation among the three photometric modes to the switching operation among the combination of the photometric modes.

In this embodiment, when the operations of these buttons are set to the switching operation in the three photometric modes corresponding to the default state, the display controller 240 displays alphabets of three photometric modes on the monitor 400.

Figure 4:
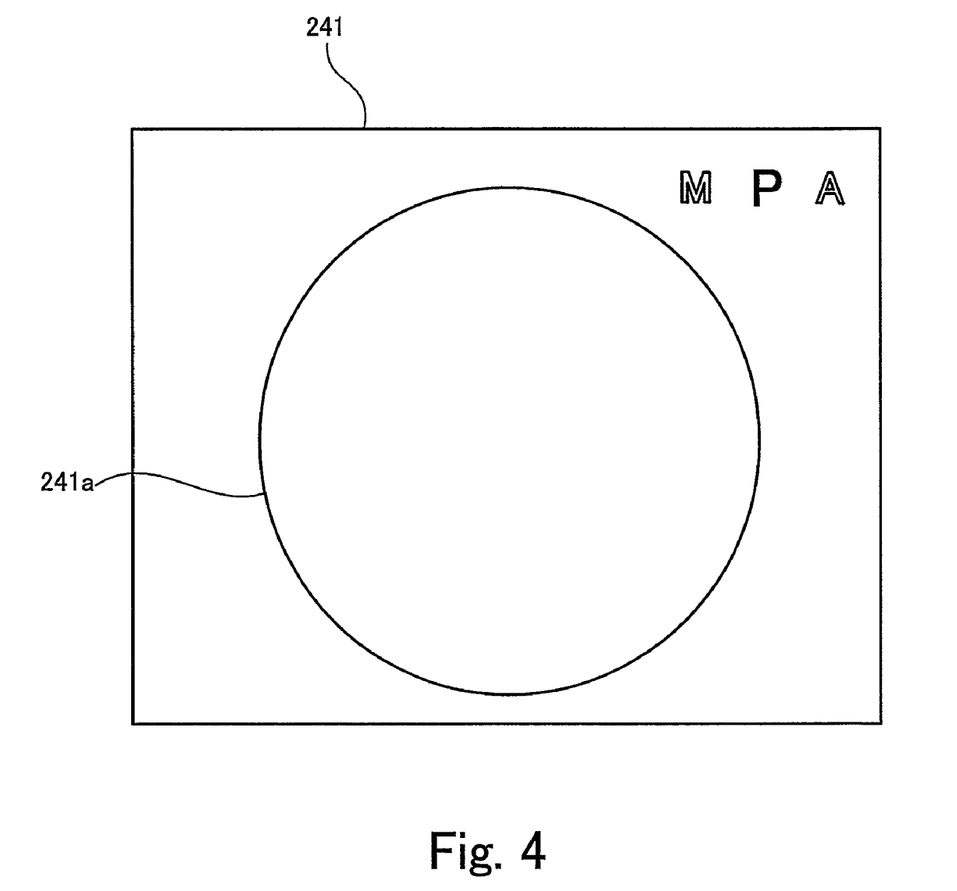
FIG. 4 is a schematic diagram showing a display section when a switching operation is set to switching between three photometric modes in which operation of each button corresponds to a default state.

FIG. 4 is a schematic diagram showing a display screen when operations of the buttons are switching operations between the three photometric modes corresponding to the default state.

In the display screen 241 shown in FIG. 4, three alphabets "M", "P" and "A" respectively showing three photometric modes are displayed in the upper right positions in the drawing in the central circular region 241*a* on which a moving image is displayed. Among these three alphabets, the one which corresponds to the currently set photometric mode is displayed in a colored character, those of alphabets corresponding to other photometric modes. In the example shown in FIG. 4, like the example in FIG. 3, the peak photometric mode is currently set, and only "P" showing the peak photometric mode is displayed in a colored character.

In this embodiment, a combination of photometric modes can be reset as many times as desired. A combination can be reset by pushing the light source device-side second operation button 360 of the light source device 300 during shooting. When a combination of photometric modes is reset, the serial number stored in the EEPROM 150 of the scope 100 is renewed to a new serial number corresponding to the new combination.

In this embodiment, when the power of the endoscope apparatus 10 is turned ON, if the serial number is stored in the EEPROM 150 of the scope 100, the processor-side CPU 210 reads the serial number, and automatically sets a combination of photometric modes corresponding to the serial number. When the serial number is not stored in the EEPROM 150, on the other hand, the processor-side CPU 210 sets the default state. The series of processing in which a combination of photometric modes is automatically set based on the serial number in the EEPROM 150 corresponds to one example of the automatically selecting mode according to the present invention.

With this processing, if a user sets a desired combination of photometric modes at the time of shooting using a scope, it is unnecessary to newly set a combination of photometric modes when shooting next time using that scope, which reduces a burden of the user.

If a user desires to change a combination of photometric modes which was automatically set when start shooting, a combination of photometric modes is set by pushing the light source device-side second operation button 360 by the user. A series of processing for setting a combination of photometric modes through the user's operation corresponds to one example of the operation selecting mode according to the present invention.

According to the endoscope apparatus 10 of the embodiment as described above, a user may carry out the switching operation in the range of a desired combination of photometric modes, and it is possible to easily switch the photometric mode.

In this embodiment, the serial number corresponding to a combination of photometric modes which is once set is stored in the EEPROM 150 of the scope 100, and at the time of next shooting operation using the scope 100, the combination of photometric modes corresponding to that serial number is automatically set. However, the method for storing a once-set combination of photometric modes and for automatically setting a combination of photometric modes when shooting next time is not limited to the method in this embodiment, and another method which will be described below may be employed.

The other method for storing a set combination of photometric modes and for automatically setting a combination of photometric modes will be described below. Even if this method is employed, a structure of the endoscope apparatus itself is the same as that of the former method. Therefore, this other method will be described also with reference to FIG. 1.

According to the former method of the automatic setting operation of the embodiment, if a combination of photometric modes is set for a certain scope, the last combination is automatically set when shooting next time using that scope. The other method is different from the former method in that if a combination of photometric modes is set for a scope of a certain model, the last combination is automatically set when shooting next time using a scope of that model. That is, according to the other method, even if a scope in which a combination of photometric modes is set is different from a scope which is used this time, if the model of the scopes is identical, the combination of the photometric modes is automatically set. The model corresponds to one example of kind of machine according to the present invention. The invention is not limited to this mode, and a kind of machine may be a kind of scopes which are classified based on subjects to be shot such as an upper alimentary canal scope or a lower alimentary canal scope, or may be a kind of scopes which are classified based on a structure such as a scope with an optical zoom and a scope without an optical zoom.

According to this other method, a serial number corresponding to a once-set combination of photometric modes is stored in the processor-side memory 220 instead of the EEPROM 150 of the scope 100. When the serial number is stored in the processor-side memory 220, the serial number is stored in association with a model of the scope 100. A model of a scope 100 is previously stored in the EEPROM 150 of the scope 100 on the side of a manufacturer. The EEPROM 150 in this other method corresponds to one example of the model storing section according to the present invention, and the processor-side memory 220 corresponds to one example of the model-associated mode storing section according to the present invention.

For the scope 100 or another scope of the same model, a combination of photometric modes is automatically set in the following manner when shooting next time. If power of the endoscope apparatus 10 is turned ON, the processor-side CPU 210 reads a model number of the scope from the EEPROM of the scope. Next, the processor-side CPU 210 searches in the processor-side memory 220 using the model number and reads a serial number corresponding to the model number, and automatically sets a combination of photometric modes corresponding to that serial number. When a serial number corresponding to that model number is not stored in the processor-side memory 220, the processor-side CPU 210 sets to the default. The series of processing for automatically setting a combination of photometric modes based on a model number in the EEPROM 150 corresponds to the model-associated selection mode according to the present invention.

With this method also, if a user sets a desired combination of photometric modes at the time of shooting using a certain scope, it is unnecessary to newly set the combination of photometric modes when shooting next time using the same scope or a different scope of the same model, and this reduces a burden of the user.

Although the example in which the invention is applied to the endoscope apparatus has been described above, the invention is not limited to this, and the invention can generally be applied to an image taking apparatus in which a picture is taken while adjusting a shooting condition by photometry and photometric modes are switched cyclically.

Although the endoscope apparatus 10 having the detachable scope 100 has been described as the one embodiment of the image taking apparatus of the invention, the invention is not limited to this. A scope may be fixed to the image taking apparatus of the invention for example.

Although the combination of the aperture 320 and the light source device-side CPU 330 which moves the aperture 320 has been described as the one example of the condition adjuster according to the present invention, the invention is not limited to this. The condition adjuster of the invention may adjust a shutter speed of an electronic shutter in a CCD, or may adjust a gain of automatic gain control in a CDS/AGC circuit.

What is claimed is:

1. An image taking apparatus comprising: a shooting section which takes an image of a subject to obtain a shot image; a photometric section which has three or more photometric modes in which brightness of the obtained shot image is determined based on brightness of each portion of the obtained shot image or brightness of a predetermined portion of the obtained shot image, by using different three or more calculation schemes respectively, any of the different three or more calculation schemes being applicable to the obtained shot image;
   a condition adjuster which adjusts a shooting condition affected by brightness of the shot image, based on the brightness measured by the photometric section;
   a mode selector which selects, in accordance with a selecting operation of a user, two or more photometric modes in accordance with a selecting operation from the three or more photometric modes of the photometric section; and
   a mode switcher which causes the photometric section to execute one of the two or more photometric modes selected by the mode selector, and cyclically switches the one of the two or more photometric modes among the two or more photometric modes in response to a switching operation of the user for instructing switching of the photometric mode,
   wherein the three or more photometric modes include at least an average photometry mode in which an average of brightness of all portions of the obtained shot image is determined as the brightness of the obtained shot image, and a peak photometry mode in which brightness of a relatively high brightness portion of the obtained shot image is determined as the brightness of the obtained shot image, and
   wherein the three or more photometric modes further include a mix photometric mode in which determined as the brightness of the obtained shot image is brightness that is obtained by multiplying the brightness of the obtained shot image determined by the average photometry mode and the brightness of the obtained shot image determined by the peak photometry mode by predetermined weights respectively and adding the two brightness multiplied by the predetermined weights.

2. The image taking apparatus according to claim 1, further comprising:
   a light source; and
   a light-introducing section which introduces light emitted from the light source to the subject,
   wherein the condition adjuster adjusts an amount of light passing through any of optical paths extending from the light source to the shooting section through the subject.

3. The image taking apparatus according to claim 1, further comprising:
   a dual-purpose operating element used for both the selecting operation and the switching operation, and
   an operation changing section which changes operation of the dual-purpose operating element between the selecting operation and the switching operation, in response to a changing operation for instructing change of operation of the dual-purpose operating element.

4. The image taking apparatus according to claim 1, wherein the mode switcher allows the photometric section to execute one of the three or more photometric modes, in response to an expansion operation for instructing expansion of a range of switchable photometric modes, and changes the switching of the one of the photometric modes by the switching operation to a cyclical switching between the three or more photometric modes.

5. The image taking apparatus according to claim 1, further comprising a display section which displays the shot image obtained by the shooting section, which also displays the photometric modes selected by the mode selector, and which displays the photometric mode executed by the photometric section among the selected photometric modes in a display mode different from that of other photometric modes.

6. The image taking apparatus according to claim 1, further comprising a body having at least the photometric section and the mode selector, and
   a scope which is detachably attached to the body and which has at least the shooting section and a mode storing section which stores the photometric modes selected by the mode selector,
   wherein when the scope is attached to the body, the mode selector captures the photometric modes stored in the mode storing section as photometric modes selected by the mode selector.

7. The image taking apparatus according to claim 6, wherein the mode selector includes an operation selecting mode for selecting photometric modes in accordance with the selecting operation, and an automatically selecting mode for capturing the photometric modes stored in the mode storing section as photometric modes selected by the mode selector, and
   wherein the operation selecting mode and the automatically selecting mode can be switched to each other by operation.

8. The image taking apparatus according to claim 1, further comprising: a body having at least the photometric section and the mode selector; and
   a scope which has at least the shooting section and which is detachably attached to the body, the scope having a model storing section which stores a model of the scope,
   wherein the body has a model-associated mode storing section which stores photometric modes selected by the mode selector in association with a model of the scope attached to the body, and
   wherein when the body is attached to the scope, the mode selector captures the photometric modes which are stored in the model-associated mode storing section associated with the same model as that of the scope, as the photometric modes selected by the mode selector.

9. The image taking apparatus according to claim 8, wherein the mode selector includes an operation selecting mode for selecting photometric modes in accordance with the selecting operation, and a model-associated selection mode for capturing the photometric modes stored in the model-associated mode storing section as the photometric modes selected by the mode selector, and
   wherein the operation selecting mode and the model-associated selection mode can be switched to each other by operation.

* * * * *